United States Patent [19]
Thiruvengadam et al.

[11] Patent Number: 5,728,827
[45] Date of Patent: Mar. 17, 1998

[54] PROCESS FOR THE SYNTHESIS OF AZETIDINONES

[75] Inventors: Tiruvettipuram Kannapan Thiruvengadam, Edison; Timothy McAllister, Fords; Chou-Hong Tann, Berkeley Heights, all of N.J.

[73] Assignee: Schering Corporation, Kenilworth, N.J.

[21] Appl. No.: 578,594

[22] PCT Filed: Jul. 1, 1994

[86] PCT No.: PCT/US94/07291

§ 371 Date: Jan. 4, 1996

§ 102(e) Date: Jan. 4, 1996

[87] PCT Pub. No.: WO95/01961

PCT Pub. Date: Jan. 19, 1995

Related U.S. Application Data

[63] Continuation-in-part of Ser. No. 89,357, Jul. 9, 1993, abandoned.

[51] Int. Cl.[6] .............. C07D 205/08; C07D 205/085; C07D 205/12
[52] U.S. Cl. .............. 540/200; 540/357; 540/358; 540/360; 540/361; 540/362; 540/363; 540/364; 540/203
[58] Field of Search .............. 540/200, 357, 540/359, 360, 361, 362, 363, 364

[56] References Cited

U.S. PATENT DOCUMENTS 4,876,365  10/1989  Kirkup et al. .............. 540/200

FOREIGN PATENT DOCUMENTS 333268    9/1989   European Pat. Off. .
415487    3/1991   European Pat. Off. .
WO92/05972  2/1993  WIPO .

OTHER PUBLICATIONS

Aldrich Chemical Catalog. p. 191 (1994).

Ho, *J. Am. Chem. Soc.*, 106 (1984), pp. 4819–4825.

Calvin *J. Chem. Soc., Chem. Commun.*, (1985), pp. 539–540.

Bringman *Synthesis*, (Oct., 1991), pp. 829–831.

Corriu, et al., *Tetrahedron*, 39, No. 6 (1983), pp. 999–1009.

Bouzard, et al, *Tetrahedron Let.*, 29,No. 16 (1988), pp. 1931–1934 (1985), pp. 539–540.

Salzmann, et al. *J.Am. Chem. Soc.*, 102 (1980), pp. 6161–6163.

Condensed Chemical Dictionary, 10th Edition (1980) p. 48.

*Primary Examiner*—Mark L. Berch
*Attorney, Agent, or Firm*—Anita W. Magatti

[57] ABSTRACT

This invention provides a process for preparing azetidinones useful as intermediates in the synthesis of penems and as hypocholesterolemic agents, particularly for azetidinones substituted in the C-3 and C-4 positions and optionally substituted at the ring nitrogen, comprising reacting a β-(substituted-amino)amide, a β-(substituted-amino)acid ester, or a β-(substituted-amino)thiolcarbonic acid ester with a silylating agent and a cyclizing agent.

12 Claims, No Drawings

PROCESS FOR THE SYNTHESIS OF AZETIDINONES

The present application is the United States national application cooresponding to International Application No. PCT/US 94/07291, filed Jul. 1, 1994 and designating the United States, which PCT application is in turn a continuation-in-part of U.S. application Ser. No. 08/089,357, filed Jul. 9, 1993, abandoned, the benefit of which applications are claimed pursuant to the provisions of 35 U.S.C. 120, 363 and 365 (C).

BACKGROUND

This invention relates to a process for producing azetidinones useful as hypocholesterolemic agents and as intermediates for the synthesis of penems.

WO 93/02048 discloses stereoselective processes for producing azetidinones. One process for preparing azetidinones wherein the substituents at the C-3 and C-4 positions have trans relative stereochemistry comprises cyclizing a hydroxyamide prepared from a carboxylic acid, an aidehyde and an amine in a process using an oxazolidinone as a chiral auxiliary. The disclosed process comprises the following steps:

(a) reacting a carboxylic acid with a chlorinating agent;
(b) deprotonating a chiral oxazolidinone, preferably R-(+)-4-benzyloxazolidinone, with a strong base or a tertiary amine base and treating the resulting anion with the product of step (a);
(c) enolizing the product of step (b) with either:
 (i) a dialkylboron triflate and a tertiary amine base; or
 (ii) TiCl$_4$ and tetramethylethylenediamine (TMEDA) or a mixture of TMEDA and triethylamine, then condensing with an aldehyde;
(d) hydrolyzing the product of step (c) with a base and hydrogen peroxide;
(e) condensing the product of step (d) with an amine by treating with a dehydrative coupling agent, optionally adding an activating agent; and
(f) cyclizing the product of step (e) by reacting the product of step (e) with:
 (i) a dialkylazodicarboxylate and a trialkylphosphine; or
 (ii) a di- or tri-chiorobenzoyl chloride, an aqueous solution of a base and a phase transfer catalyst, then treating the resulting di- or tri-chlorobenzoate with an aqueous solution of a base and a phase transfer catalyst; or
 (iii) a dialkylchlorophosphate, an aqueous solution of a base and a phase transfer catalyst; or
 (iv) a di- or tri-chlorobenzoyl chloride and a metal hydride.

In another process of WO 93/02048, an azetidinone having trans relative stereochemistry as described above is prepared by cyclizing a β-aminoamide derivative prepared from a carboxylic acid and an imine in a process using an oxazolidinone, preferably S-phenyl-oxazolidinone, as a chiral auxiliary. This process comprises the steps:

(a) reacting a carboxylic acid with a chlorinating agent;
(b) deprotonating a chiral oxazolidinone, preferably S-phenyl-oxazolidinone, with a strong base or a tertiary amine base and treating the resulting anion with the product of step (a);
(c) enolizing the product of step (b) with TiCl$_4$ and tetramethyl-ethylenediamine (TMEDA), then condensing with an imine; and
(d) cyclizing the product of step (c) by treating with a strong non-nucleophilic base, preferably an alkali metal bistrimethylsilylamide.

SUMMARY OF THE INVENTION

This invention provides a simple, high-yielding process for producing azetidinones under neutral conditions. Azetidinones are useful as hypocholesterolemic agents, as disclosed in WO 93/02048 and PCT International Application No. PCT/US94/00421, and are also useful as intermediates in the synthesis of penems, a known group of antibacterials. This process is applicable for preparing azetidinones which are optionally mono-, di- or unsubstituted at each of the C-3 and C-4 positions and substituted at the ring nitrogen. The stereochemistry of C-3, C-4-disubstituted azetidinones prepared by this process is dependent on the starting material: racemic, stereospecific or enantiomeric compounds can be obtained when the corresponding starting materials are used. In particular, this process is useful for the stereospecific preparation of azetidinones substituted in the C-3 and C-4 positions, and optionally substituted at the ring nitrogen.

In its broadest aspect, this invention relates to a process for preparing an azetidinone comprising reacting a β-(substituted-amino)-amide, a β-(substituted-amino)acid ester, or a β-(substituted-amino)-thiolcarbonic acid ester with a silylating agent and a cyclizing agent.

More particularly, this invention relates to a process for preparing an azetidinone comprising reacting a silylating agent and a fluoride ion catalyst cyclizing agent with a suitably protected compound selected from the group consisting of i) a β-(substituted-amino)amide, wherein the carbamoyl portion is B—C(O)—, wherein B is a deprotonated chiral auxiliary selected from the group consisting of

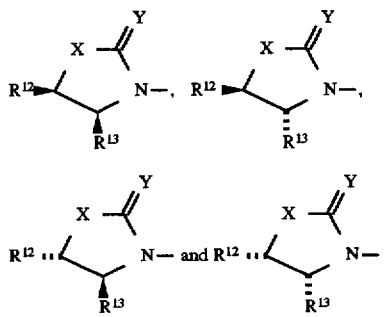

wherein X is —O—, —S— or —N(C$_1$–C$_6$alkyl)-; Y is =O or =S; and R$^{12}$ and R$^{13}$ are independently selected from the group consisting of C$_1$–C$_6$alkyl, phenyl, naphthyl, substituted phenyl, substituted naphthyl, lower alkoxy-carbonyl and benzyl, wherein the substituents on the phenyl and naphthyl are 1–3 substituents selected from the group consisting of lower alkyl, phenyl and benzyl, or wherein one of R$^{12}$ or R$^{13}$ is as defined above and the other is hydrogen; or B is (R$^{14}$)(R$^{15}$)N—, wherein R$^{14}$ and R$^{15}$ are independently selected from the group consisting of lower alkyl, aryl and benzyl;

ii) a β-(substituted-amino)acid ester, wherein the carboxylic acid ester portion is R$^{14}$—S—C(O)—, wherein R$^{14}$ is lower alkyl, aryl or benzyl; and iii) a β-(substituted-amino)thiolcarbonic acid ester, wherein the thiolcarbonic acid ester portion is R$^{14}$—S—C(O)—, wherein R$^{14}$ is lower alkyl, aryl or benzyl.

Alternatively, when B is a deprotonated chiral auxiliary as defined above, the cyclization can be effected by the addition of a monovalent salt of the chiral auxiliary, i.e., a compound of the formula

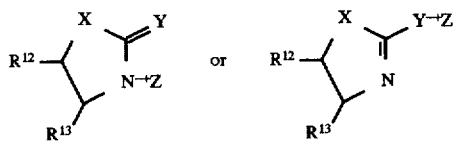

wherein X, Y, $R^{12}$ and $R^{13}$ are as defined above and Z is selected from the group consisting of quaternary ammonium cations, such as arylalkyl-alkylammonium, aryl-alkylammonium and tetraalkylammonium, or mixtures thereof, and alkali metals. Examples of arylalkyl-alkylammonium groups are benzyltriethyl-ammonium and benzyl-trimethylammonium; examples of aryl-alkyl-ammonium are phenyltriethylammonium and phenyltrimethyl-ammonium; typical tetraalkylammonium groups contain alkyl groups of 1–6 carbon atoms, e.g., tetra n-butylammonium; and typical alkali metals are sodium, potassium, cesium and lithium.

The process using a starting material wherein the β-(substituted-amino)amide comprises a deprotonated chiral auxiliary as defined above in (i) can alternatively be used with a non-chiral auxiliary, i.e., an auxiliary as defined above wherein each of $R^{12}$ and $R^{13}$ are hydrogen. The process employing a non-chiral auxiliary in the starting material can employ either a fluoride ion catalyst or a salt of a chiral or non-chiral auxiliary for cyclization. Also, a salt of a non-chiral auxiliary can be used as a cyclizing agent in a process using a starting material containing a chiral auxiliary.

A particularly preferred embodiment of this invention relates to a process for preparing an azetidinone, especially a stereospecific azetidinones as disclosed in WO 93/02048 and PCT/US94/00421, represented by structural formula I

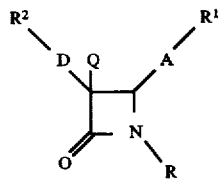

wherein

Q is hydrogen, lower alkyl; phenyl-$(CH_2)_{0-3}$- or (W-substituted)phenyl-$(CH_2)_{0-3}$;

R is phenyl, W-substituted phenyl, naphthyl, W-substituted naphthyl, benzodioxolyl, heteroaryl, W-substituted heteroaryl, benzofused heteroaryl and W-substituted benzofused heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof;

$R^1$ and $R^2$ are independently selected from H or R;

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkylenedioyl, lower alkyl lower alkylenedioyl, allyloxy, —$CF_3$, —$OCF_3$, benzyl, $R^3$-benzyl, benzyloxy, $R^3$-benzyloxy, phenoxy, $R^3$-phenoxy, dioxolanyl, $NO_2$, —$NR^4R^5$, $NR^4R^5$(lower alkyl)-, $NR^4R^5$(lower alkoxy)-, OH, halogeno, —NHC(O)$OR^6$, —NHC(O)$R^6$, $R^7O_2$SNH—, ($R^7O_2S)_2N$—, —$S(O)_2NH_2$, —$S(O)_{0-2}R^4$, tert-butyldimethyl-silyloxymethyl,

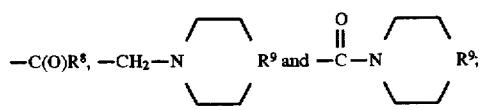

A and D are independently a bond; $C_3$–$C_6$ cycloalkylene; $C_1$–$C_{10}$ alkylene; $C_1$–$C_{10}$ alkenylene; $C_1$–$C_{10}$ alkynylene; an alkylene, alkenylene or alkynylene chain as defined substituted by one or more substituents independently selected from the group consisting of phenyl, W-substituted phenyl, heteroaryl and W-substituted heteroaryl, wherein heteroaryl is as defined above; an alkylene, alkenylene or alkynylene chain as defined interrupted by one or more groups independently selected from the group consisting —O—, —S—, —SO—, —$SO_2$—, —$NR_8$, —C(O)—, $C_3$–$C_6$ cycloalkylene, phenylene, W-substituted phenylene, heteroarylene and W-substituted heteroarylene; or an interrupted alkylene, alkenylene or alkynylene chain as defined substituted by one or more substituents independently selected from the group consisting of phenyl, W-substituted phenyl, heteroaryl and W-substituted heteroaryl; or $R^2$-D is selected from the group consisting of halogeno, OH, lower alkoxy, —OC(O)$R^6$, —$NR^4R^5$, —SH and —S(lower alkyl);

$R^3$ is 1–3 groups independently selected from the group consisting of lower alkyl, lower alkoxy, —COOH, $NO_2$, —$NR^4R^5$, OH or halogeno;

$R^4$ and $R^5$ are independently selected from H and lower alkyl;

$R^6$ is lower alkyl, phenyl, $R^3$-phenyl, benzyl or $R^3$-benzyl;

$R^7$ is OH, lower alkyl, phenyl, benzyl, $R^3$-phenyl or $R^3$-benzyl; $R^8$ is H, OH, alkoxy, phenoxy, benzyloxy,

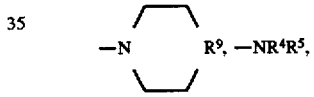

lower alkyl, phenyl or $R^3$-phenyl;

$R^9$ is —O—, —$CH_2$—, —NH— or —N(lower alkyl)-;

or Q and $R^2$—D— together form the group

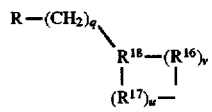

wherein $R^{18}$ is

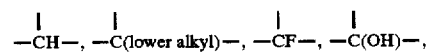
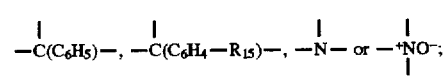

$R^{16}$ and $R^{17}$ are independently selected from the group consisting of —$CH_2$—, —CH(lower alkyl)-, —C(di-lower alkyl)-, —CH=CH— and —C(lower alkyl)=CH—; or $R^{18}$ together with an adjacent $R^{16}$, or $R^{18}$ together with an adjacent $R^{17}$, form a —CH=CH— or a —CH=C(lower alkyl)- group;

u and v are independently 0, 1, 2 or 3, provided both are not zero; provided that when $R^{16}$ is —CH=CH— or —C(lower alkyl)=CH—, v is 1; provided that when $R^{17}$ is —CH=CH— or —C(lower alkyl)=CH—, u is 1; provided that when v is 2 or 3, the $R^{16}$'s can be the same or different; and provided that when u is 2 or 3, the $R^{17}$s can be the same or different; and q is 0, 1, 2, 3, 4, 5 or 6; comprising reacting a compound of formula II

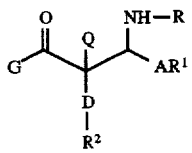  II wherein A, D, Q, R, $R^1$ and $R^2$ are as defined above and G is B, $(R^{14})$—O— or $(R^{14})$—S—, wherein B and $R^{14}$ are as defined above, with a silylating agent and a fluoride ion catalyst cyclizing agent or, when B is a chiral auxiliary, with a silylating agent and a salt of said chiral auxiliary, provided that where substituents A, D, Q, R, $R^1$ and $R^2$ include substituents selected from the group consisting of —$NH_2$, —SH and —OH, said substituents are suitably protected prior to reaction with the silylating agent.

A particularly preferred embodiment of the present invention relates to the preparation of compounds of formula I wherein Q is hydrogen and the substitutents $R^2$—D— and $R^1$—A— have trans relative stereochemistry, wherein said process comprises reacting a compound of formula IIa

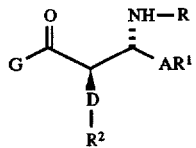  IIa wherein A, D, R, $R^1$ and $R^2$ are as defined above and G is B, $(R^{14})$—O— or $(R^{14})$—S—, wherein B and $R^{14}$ are as defined above, with a silylating agent and a fluoride ion catalyst cyclizing agent or, when B is a chiral auxiliary, with a silylating agent and a salt of said chiral auxiliary, provided that where substituents A, D, R, $R^1$ and $R^2$ include substituents selected from the group consisting of —$NH_2$, —SH and —OH, said substituents are suitably protected prior to reaction with the silylating agent.

DETAILED DESCRIPTION

As used herein, the terms β-(substituted-amino)amide, β-(substituted-amino)acid ester, and β-(substituted-amino) thiolcarbonic acid ester refer to β-aminoamides, β-aminoacid esters, and β-aminothiolcarbonic acid esters refer to secondary amines, that is, compounds wherein the nitrogen is joined to the β-carbon, to a hydrogen molecule, and to a non-hydrogen substituent.

"Aryl" means phenyl, W-substituted phenyl, naphthyl or W-substituted naphthyl.

As used herein, the term "lower alkyl" means straight or branched alkyl chains of 1 to 6 carbon atoms and "lower alkoxy" similarly refers to alkoxy groups having 1 to 6 carbon atoms;

"Alkenyl" means straight or branched carbon chains having one or more double bonds in the chain, conjugated or unconjugated, and alkadienyl refers to chains having two double bonds in the chain; similarly, "alkynyl" means straight or branched carbon chains having one or more triple bonds in the chain.

Where an alkyl, alkenyl or alkynyl chain joins two other variables and is therefore bivalent, the terms alkylene, alkenylene and alkynylene are used.

"Cycloalkyl" means a saturated carbon ring of 3 to 6 carbon atoms, while "cycloalkylene" refers to a corresponding bivalent ring, wherein the points of attachment to other groups include all positional isomers.

"Halogeno" refers to fluorine, chlorine, bromine or iodine radicals.

"Heteroaryl" includes all positional isomers for a given heteroaryl group as defined above, for example 2-pyridyl, 3-pyridyl and 4-pyridyl. Benzofused heteroaryl refers to radicals formed by the bonding of a benzene radical to adjacent carbon atoms on a heteroaryl ring; examples are indolyl, quinolyl, quinazolinyl, quinoxalinyl, benzotriazolyl, indazolyl, benzoxazolyl, benzothienyl and benzofuranyl.

"Phenylene" means a bivalent phenyl group bound in an ortho, meta or para orientation and "heteroarylene" similarly means a bivalent heteroaryl group, including all positional isomers.

"(Lower alkoxyimino)lower alkyl" refers to the group ($C_1$-$C_6$ lower alkoxy)-N=CH-($C_1$-$C_5$ lower alkyl). "Lower alkylenedioyl" means radicals of the formula —OC(O) $(CH_2)_{1-4}$C(O)OH, while "lower alkyl lower alkylenedioyl" means radicals of the formula —OC(O)$(CH_2)_{1-4}$C(O)O- (lower alkyl).

$R^3$-benzyl and $R^3$-benzyloxy refer to benzyl and benzyloxy radicals which are substituted on the phenyl ring.

The carbon chains as defined in A and D, when substituted by optionally substituted phenyl or heteroaryl groups, may include independent substitution on different carbon atoms, di-substitution on one carbon atom, or both. One skilled in the art will recognize that the number of double or triple bonds present, the replacement of carbon atoms in the chain and the presence of substitutents on the carbon atoms in the chain are all dependent on the length of the chain: shorter carbon chains cannot accommodate as many double or triple bonds, carbon replacements or substituents as longer carbon chains can. In general, unsaturated carbon chains contain 1 to 4 double or triple bonds, conjugated or non-conjugated. Where carbon atoms are replaced, 1 to 4 replacement groups can be present. Similarly, when carbon atoms in the chain are substituted, 1 to 4 substituents can be present.

Examples of alkylene chains in A and D are methylene, ethylene, propylene, butylene and decylene.

Examples of unsaturated A and D groups are ethenylene and acetylene.

Examples of A and D groups wherein the carbon atoms in the chain are replaced are —$CH_2CH_2O$—, —$OCH_2CH_2$—, —$CH_2O$—, —$CH_2CH_2CH_2O$—, —$CH_2$—O—$CH_2$—, —$CH_2CH_2$—O—$CH_2$, —$CH_2CH_2$—NH—, —$CH_2CH_2$—N($CH_3$)— and —O—$CH_2C(O)$—NH—.

Azetidinones prepared by this process, and in particular compounds of formula I, may have at least two asymmetrical carbon atoms and therefore the preparation of all isomers, including diastereomers and rotational isomers, is contemplated. The compounds prepared by this invention include d and I isomers in both pure form and in admixture, including racemic mixtures. Isomeric compounds prepared by this invention may also include geometric isomers, e.g. when A or D in compounds of formula I contains a double bond.

The order of addition of the components of this process is not critical to the preparation of the azetidinone product. For example, the starting β-(substituted-amino)amide, β-(substituted-amino)acid ester, or β-(substituted-amino) thiolcarbonic acid ester can first be reacted with the silylating agent and then reacted with the cyclizing agent, or the starting compound can be added to a mixture of the silylating agent and the cyclizing agent.

Silylation is effected by reacting the starting material with a silyl-enol ether silylating agent such as bistrimethylsilyl acetamide (BSA), N-methyl-O-trimethylsilyl acetamide or iso-propenyloxy trimethylsilane, preferably BSA, in a suitable inert organic solvent at 0° C. to 110° C., preferably at about 20° C. to 90° C., and more preferably at ambient temperature (e.g., about 25° C.). The reaction is preferably carried out in a dry, inert atmosphere, e.g., the solvent is dried, typically with molecular sieves, and the reaction is carried out under nitrogen. When the silylation and cyclization are done sequentially, i.e., the silylating agent is reacted with the starting material first, the silylation reaction can be allowed to continue for up to about two hours, but preferably the cyclization step is carried out immediately after silylation, or the silylating agent and the cyclizing agent are added simultaneously.

Those skilled in the art will recognize that for cyclization to proceed as desired, —NH$_2$, —SH and —OH substituents present on the β-(substituted-amino)amide, a β-(substituted-amino)acid ester, or a β-(substituted-amino)thiolcarbonic acid ester starting material must be converted to groups which will not be silylated, either preferentially or in addition to silylation of the substituted-amino portion of the molecule (i.e., —NH—R in formula II). Suitable protecting groups well known in the art include for —NH$_2$: t-butyldimethylsilyl, benzyl, benzoyl and t-butoxycarbonyl; for —SH: triphenylmethyl; and for —OH: lower alkoxy, e.g., methoxy, benzyloxy and t-butyldimethylsilyl.

The source of the fluoride ion used to catalyze the intra-molecular cyclization is typically a quaternary alkyl-, aryl-alkyl- or arylalkyl-alkylammonium fluoride salt or a hydrate thereof, or a mixture thereof, wherein alkyl-, arylalkyl- or arylalkyl-alkylammonium are as defined above for Z, or is an alkali metal fluoride salt or a hydrate thereof, such as cesium fluoride or potassium fluoride. When a hydrated quaternary ammonium fluoride salt is used, the reagent is added in a catalytic amount, i.e., about 1 to about 20 mole percent, preferably about 5 mole percent, and when an anhydrous quaternary ammonium fluoride salt is used, it can be added in a catalytic up to a stoichiometric amount. When an alkali metal fluoride salt is used, it is added in catalytic amount up to a stoichiometric amount compared to the starting β-amino compound, depending on the solubility of the reagent in the solvent used (higher solubility requires less reagent). If added to the reaction mixture after the silylation agent, the fluoride reagent is added directly to the reaction mixture resulting from silylation, and is reacted at about 0° C. to 110° C., preferably about 20° C. to 60° C., for about 0.5 to about 6 hours, preferably about 1 hour. When the silylation reagent and the fluoride reagent are added simultaneously, the reaction is conducted under similar conditions.

Alternatively, for cyclizing compounds wherein the starting β-amino compound contains a chiral auxiliary, a salt of the chiral auxiliary as defined above may be used instead of the fluoride ion to catalyze the reaction. The chiral auxiliary-containing β-amino compound is reacted at room temperature up to reflux temperature for 1 hour with a silylating reagent as described above under an inert atmosphere, e.g., N$_2$, in a suitable inert solvent. The chiral auxiliary salt can be added to the reaction mixture at the same time as the silylating agent, or it can be added directly to the reaction mixture resulting from silylation in a catalytic amount or in a stoichiometric amount compared to the starting β-amino compound, and the mixture is reacted at about 0° C. to 110° C., preferably about 20° to 60° C. for an additional hour.

The azetidinone resulting from either the fluoride ion or chiral auxiliary salt process can be purified by appropriate standard procedures such as column chromatography or crystallization.

The term "suitable inert organic solvent" as used above means any organic solvent or combination of solvents that is unreactive in the reaction being conducted and is a solvent for the reactants. Typical suitable solvents are halogenated compounds such as dichloromethane; heterocyclic compounds such as tetrahydrofuran (THF); DMSO; dimethylformamide (DMF); acetonitrile; and carbocyclic aromatics such as toluene. Preferred are toluene, THF and dichloromethane.

Starting β-(substituted-amino)amides, β-(substituited-amino)acid esters and β-(substituted-amino)thiolcarbonic acid esters are known or can be prepared by one skilled in the art using known methods. β-aminoamide compounds of formula II and IIa, wherein B is a radical of a chiral auxiliary, are disclosed in WO 93/02048.

The chiral auxiliary salt is prepared by known procedures, for example the tetra n-butylammonium salt of a 2-oxazolidinone can be prepared by deprotonating the chiral auxiliary with a strong base such as sodium hydride in an inert solvent such as THF at 0° C. for 30 minutes, then adding the tetra n-butylammonium chloride or bromide salt and stirring for an additional 30 minutes.

An especially preferred embodiment of the process of this invention comprises the reaction of a β-(substituted-amino) amide of formula IIb, i.e., a compound of formula IIa wherein G is B', a deprotonated chiral auxiliary as defined above; use of a chiral auxiliary as part of the starting β-(substituted-amino)amide is particularly desirable because the salt of the chiral auxiliary resulting from the process can be recovered for reuse. A more preferred embodiment, exemplified by the preparation of compounds of formula I wherein the C-3 and C-4 substitutents have trans relative stereochemistry, is shown in Scheme A. Said process comprises the reaction of a compound of formula IIb, wherein A, D, X, Y, R, R$^1$, R$^2$, R$^{12}$ and R$^{13}$ are as defined above, with a silylating agent and a fluoride ion to prepare a compound of formula Ia, wherein Q is hydrogen.

Scheme A:

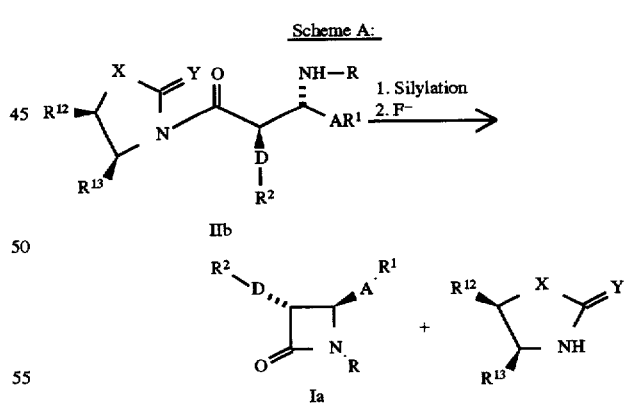

In the reaction shown in Scheme A, it is preferred that in the starting material of compound IIb, X and Y are each oxygen and R$^{12}$ is hydrogen. More preferred compounds of formula IIb are those wherein X and Y are each oxygen, R$^{12}$ is hydrogen and R$^{13}$ is phenyl, benzyl or isopropyl. A preferred silylating agent is BSA, and a preferred source of fluoride ion is tetra n-butylammonium fluoride or a hydrate thereof, preferably its trihydrate.

The following examples illustrate the process of this invention. Although the examples are directed to C-3, C-4 disubstituted compounds and the stereochemistry of the reactants and intermediates are indicated in the various depicted structural formulas in the following examples, it is to be understood that the process of this invention is operative for azetidinones regardless of stereochemistry, and involves merely the selection of reactants having the desired racemic or stereochemical configuration and the selection of reaction conditions which result in the desired configuration in the product.

Preparation 1

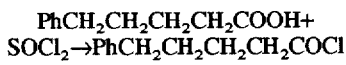

Step A: To a stirred suspension of 5-phenyl valeric acid (50 g, 281 mmol) in toluene (50 mL), add $SOCl_2$ (40 mL, 548 mmol). Heat the mixture to 90° C. in an oil bath for 3 hours. Distill off the excess $SOCl_2$ as an azeotropic mixture with toluene under reduced pressure. Again add toluene (50 mL), and distill off both toluene and any residual $SOCl_2$ under reduced pressure. Add $CH_2Cl_2$ (200 mL) to the crude acid chloride in the reaction flask and use the resulting solution directly in Step B.

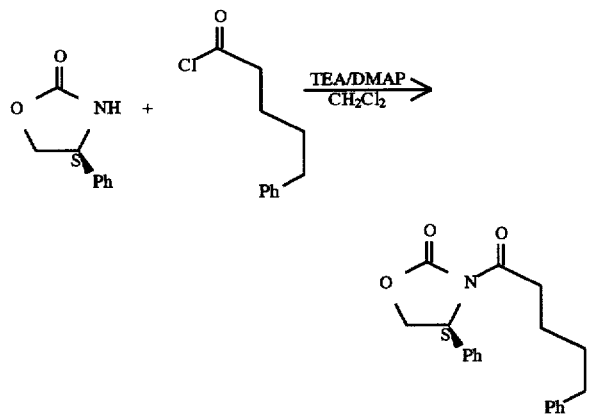

Step B: To $CH_2Cl_2$ (600 mL), add (4S)-4-phenyl-2-oxazolidinone (38.6 g, 236.8 mmol), triethylamine (TEA) (80 mL, 574 mmol) and 4-dimethyl-amino pyridine (DMAP) (2 g, 16.4 mmol). Stir the mixture and cool in an ice-bath to ~5° C. Slowly add the solution of Step A, maintaining the temperature at ~5° C. After the addition is complete, allow the mixture to warm to room temperature and stir overnight. Add water (400 mL) and stir for 30 minutes to destroy the excess acid chloride. Separate the organic layer and extract the aqueous layer with $CH_2Cl_2$ (200 mL). Combine the organic layers, wash with aqueous 2N $H_2SO_4$ (600 mL), followed by brine solution (200 mL), saturated $NaHCO_3$ (400 mL) and brine solution (200 mL). Concentrate the organic layer under reduced pressure, and dissolve the resultant residue in $CH_2Cl_2$ to a total volume of 1000 mL. Use this solution in Step C.

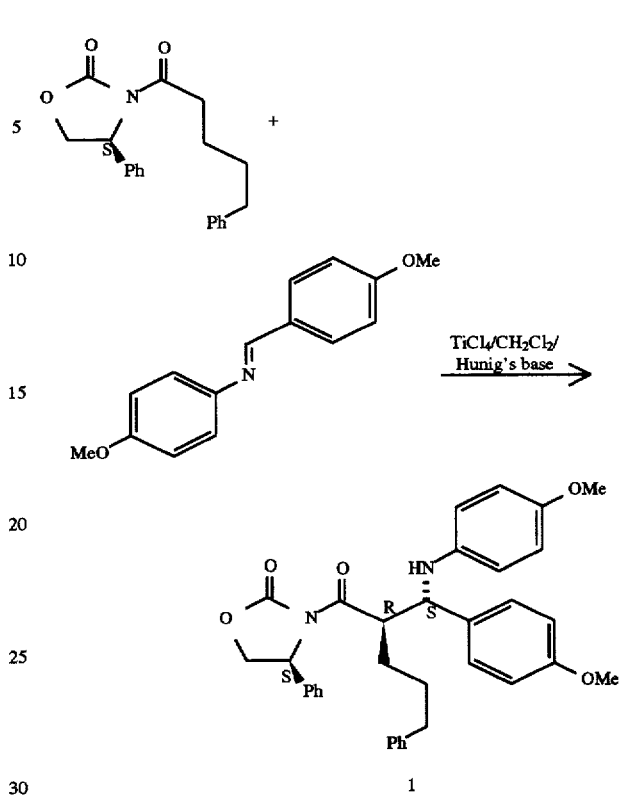

Step C: Cool a solution of the product of Step B (238 mL, 56.4 mmol) in $CH_2Cl_2$ to -20° C. to -25° C. Slowly add a 1 molar solution of $TiCl_4$ in $CH_2Cl_2$ (56 mL, 56 mmol), while maintaining the temperature below -20° C. After the addition is complete, stir for 10 min. at that temperature. Slowly add Hunig's base (N,N-diisopropylethylamine) (19.5 mL, 112 mmol); a characteristic dark-red color is observed. Stir the mixture for 30 min. at -20° to -25° C. Slowly add a solution of Schiff's base derived from anisaldehyde and p-anisidine (26.86 g, 111.5 mmol) in $CH_2Cl_2$ (200 mL) and stir for 1 hour while maintaining the temperature below -20° C. Quench the reaction by adding a solution of glacial acetic acid (18 mL) in $CH_2Cl_2$ (32 mL), maintaining the temperature below -20° C. Continue stirring for 30 min., then pour the reaction mixture into aqueous 2N $H_2SO_4$ (600 mL ) at 0° C. Stir for 30 minutes, then add ethyl acetate (EtOAc)(1 L) and stir until the organic layer separates cleanly. Separate the organic layer, extract the aqueous layer with $CH_2Cl_2$ (50 mL), combine the organic layers and wash with saturated $NaHCO_3$ solution, followed by brine solution. Concentrate the organic layer under reduced pressure and crystallize the residue from EtOAc and hexane to obtain the pure (β-amino carbonyl compound of formula 1.

EXAMPLE 1

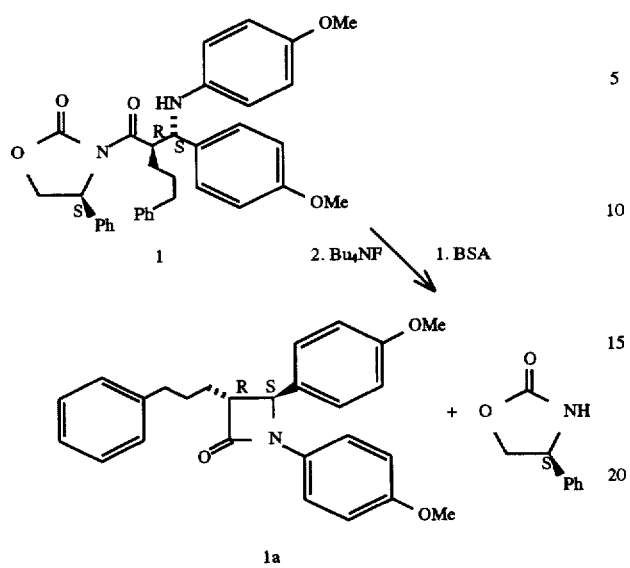

EXAMPLE 1

To a stirred suspension of the β-aminoamide of formula 1 (15 g, 26.6 mmol) in sieve-dried toluene (225 mL) at about 90° C. under a $N_2$ atmosphere, add BSA (10 mL, 40.5 mmol) and heat the reaction mixture for about one hour at about 90° C. Add tetra n-butylammonium fluoride trihydrate (420 mg, 1.33 mmol) and heat for one hour at 90° C. to obtain 10.2 g of the compound of formula Ia (96% yield), 99% de, 99.9% ee.

EXAMPLE 1A

To a stirred suspension of the β-aminoamide of formula 1 as shown in Example 1 (20 g, 35.5 mmol) in sieve-dried toluene (400 mL) at about 90° C. under a $N_2$ atmosphere, add BSA (15 mL, 60.75 mmol) and heat at about 90° C. for 2 hours. Cool to 55°–60° C., add tetra n-butylammonium fluoride trihydrate (560 mg, 1.78 mmol) and heat for 2 hours at 55°–60° C. to obtain 13.62 g of the compound of formula Ia as shown in Example 1 (96% yield), 99% de, 99.9% ee.

EXAMPLE 1B

To a stirred suspension of the β-aminoamide of formula 1 as shown in Example 1 (20 g, 35.5 mmol) in toluene (200 mL) at room temperature, add BSA (15 mL, 60.75 mmol), followed by tetra n-butylammonium fluoride trihydrate (112 mg, 0.35 mmol). Monitor the reaction progress by HPLC; after 1.5 h, obtain compound 1a (14.2 g, 99.8% yield) 99% de, 99.9% ee.

EXAMPLE 1C

To a stirred suspension of the β-aminoamide of formula 1 as shown in Example 1 (5.014 g, 8.9 mmol) in DMSO (35 mL) at room temperature, add BSA (3.8 mL, 15.2 mmol), followed by CsF (68 mg, 0.445 mmol). Monitor the reaction progress by HPLC; add additional BSA (2 mL) and stir 4 h to obtain compound 1a (2.8 g, 79% yield) 96% de, 99.9% ee.

EXAMPLE 2

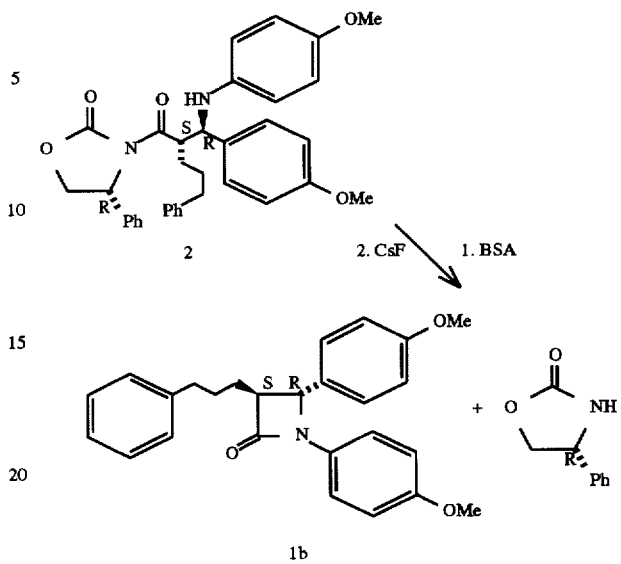

To a stirred suspension of the β-aminoamide of formula 2 (5 g, 8.9 mmol) in dry THF (75 mL), add BSA (5.4 mL, 21.85 mmol), then reflux under a $N_2$ atmosphere for 16 hours. Add anhydrous CsF (1.35 g, 8.9 mmol) and reflux for 6 hours to obtain 3.42 g of the compound of formula Ib (96% yield), 99% de.

EXAMPLE 2A

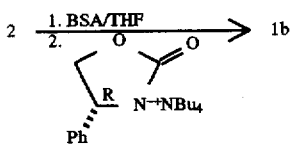

Step 1: To a stirred solution of (R)-4-phenyl-2-oxazolidinone (174 mg, 1.06 mmol) in THF (4 mL) at 0° C., add NaH (4.3 mg, 60% emulsion in oil, 0.106 mmol). Allow the temperature to rise to room temperature over 30 min., then add tetra n-butylammonium bromide (34 mg, 0.106 mmol) to the mixture and stir for another 30 min. to obtain (R)-4-phenyl-2-oxazolidinone tetra n-butylammonium salt.

Step 2: To a stirred solution of the β-aminoamide of formula 2 (0.604 g, 1.06 mmol) in sieve-dried THF (8 mL) at reflux under an $N_2$ atmosphere, add BSA (0.66 mL, 2.66 mmol). Heat to reflux for 1 h, then add a solution of the product of Step 1 (0.106 mmol) in THF (4 mL). Continue heating for 1 h to obtain the product 1b (0.37 g, 87% yield) 97% de, 99.9% ee.

In a similar manner, at reflux or at room temperature, use (S)-4-phenyl-2-oxazolidinone tetra n-butylammonium salt and compound 1 of Preparation 1 to prepare compound Ia.

We claim:

1. A process for preparing an azetidinone represented by the formula

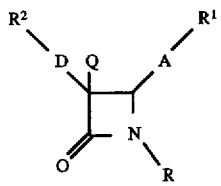

wherein

Q is hydrogen, lower alkyl, phenyl-$(CH_2)_{0-3}$- or (W-substituted)-phenyl-$(CH_2)_{0-3}$;

R is phenyl, W-substituted phenyl, naphthyl, W-substituted naphthyl, benzodioxolyl, heteroaryl, W-substituted heteroaryl, benzofused heteroaryl and W-substituted benzofused heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof;

$R^1$ and $R^2$ are independently selected from H or R;

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkylenedioyl, lower alkyl lower alkylenedioyl, allyloxy, —$CF_3$, —$OCF_3$, benzyl, $R^3$-benzyl, benzyloxy, $R^3$-benzyloxy, phenoxy, $R^3$-phenoxy, dioxolanyl, $NO_2$, —$NR^4R^5$, $NR^4R^5$(lower alkyl)-, $NR^4R^5$(lower alkoxy)-, OH, halogeno, —NHC(O)$OR^6$, —NHC(O)$R^6$, $R^7O_2$SNH—, $(R^7O_2S)_2N$—, —$S(O)_2NH_2$, —$S(O)_{0-2}R^4$, tert-butyldimethyl-silyloxymethyl, —C(O)$R^8$,

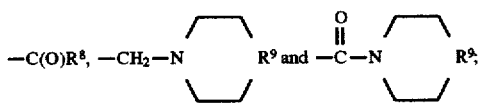

A and D are independently a bond; $C_3$-$C_6$ cycloalkylene; $C_1$-$C_{10}$ alkylene; $C_2$-$C_{10}$ alkenylene; $C_2$-$C_{10}$ alkynylene; an alkylene, alkenylene or alkynylene chain as defined substituted by one or more substituents independently selected from the group consisting of phenyl, W-substituted phenyl, heteroaryl and W-substituted heteroaryl, wherein heteroaryl is as defined above; an alkylene, alkenylene or alkynylene chain as defined interrupted by one or more groups independently selected from the group consisting of —O—, —S—, —SO—, —$SO_2$—, —$NR_8$, —C(O)—, $C_3$-$C_6$cycloalkylene, phenylene, W-substituted phenylene, heteroarylene and W-substituted heteroarylene; or an interrupted alkylene, alkenylene or alkynylene chain as defined substituted by one or more substituents independently selected from the group consisting of phenyl, W-substituted phenyl, heteroaryl and W-substituted heteroaryl; or $R^2$-D is selected from the group consisting of halogeno, OH, lower alkoxy, —OC(O) $R^6$, —$NR^4R^5$, —SH and —S(lower alkyl);

$R^3$ is 1–3 groups independently selected from the group consisting of lower alkyl, lower alkoxy, —COOH, $NO_2$, —$NR^4R^5$, OH or halogeno;

$R^4$ and $R^5$ are independently selected from H and lower alkyl;

$R^6$ is lower alkyl, phenyl, $R^3$-phenyl, benzyl or $R^3$-benzyl;

$R^7$ is OH, lower alkyl, phenyl, benzyl, $R^3$-phenyl or $R^3$-benzyl;

$R^8$ is H, OH, alkoxy, phenoxy, benzyloxy,

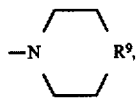

—$NR^4R^5$, lower alkyl, phenyl or $R^3$-phenyl;

$R^9$ is —O—, —$CH_2$—, —NH— or —N(lower alkyl)-;

or Q and $R^2$—D— together form the group

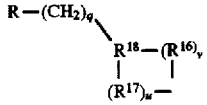

wherein $R^{18}$ is

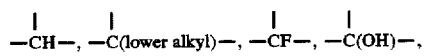

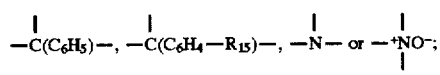

$R^{16}$ and $R^{17}$ are independently selected from the group consisting of —$CH_2$—, —CH(lower alkyl)-, —C(di-lower alkyl)-, —CH=CH— and —C(lower alkyl)=CH—; or $R^{18}$ together with an adjacent $R^{16}$, or R18 together with an adjacent $R^{17}$, form a —CH=CH— or a —CH=C(lower alkyl)- group;

u and v are independently 0, 1, 2 or 3, provided both are not zero; provided that when $R^{16}$ is —CH=CH— or —C(lower alkyl)=CH—, v is 1; provided that when $R^{17}$ is —CH=CH— or —C(lower alkyl)=CH—, u is 1; provided that when v is 2 or 3, the $R^{16}$'s can be the same or different; and provided that when u is 2 or 3, the $R^{17}$'s can be the same or different; and q is 0, 1, 2, 3, 4, 5 or 6;

comprising reacting a compound of formula II

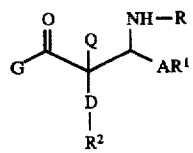

wherein A, D, Q, R, $R^1$ and $R^2$ are as defined above and G is B, wherein B is a deprotonated chiral auxiliary selected from the group consisting of

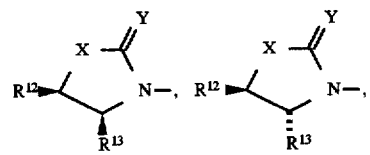

-continued

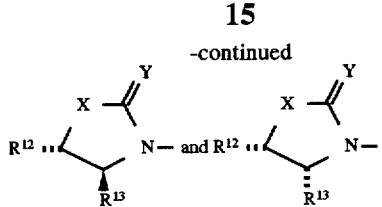

wherein X is —O—, —S— or —N($C_1C_6$alkyl)-; Y is =O or =S; and $R^{12}$ and $R^{13}$ are independently selected from the group consisting of $C_1$-$C_6$ alkyl, phenyl, naphthyl, substituted phenyl, substituted naphthyl, lower alkoxycarbonyl and benzyl, wherein the substituents on the phenyl and naphthyl are 1–3 substituents selected from the group consisting of lower alkyl, phenyl and benzyl, or wherein one of $R^{12}$ or $R^{13}$ is as defined above and the other is hydrogen; with a silylating agent and a fluoride ion catalyst cyclizing agent or, when B is a deprotonated chiral auxiliary as defined above, with a silylating agent and a salt of said chiral auxiliary, provided that where substituents A, D, Q, R, $R^1$ and $R^2$ include substituents selected from the group consisting of —$NH_2$, —SH and —OH, said substituents are suitably protected prior to reaction with the silylating agent.

2. A process for preparing an azetidinone represented by the formula

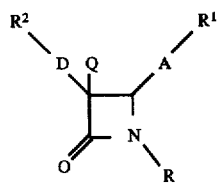

wherein

Q is hydrogen, lower alkyl, phenyl-$(CH_2)_{0-3}$- or (W-substituted)-phenyl-$(CH_2)_{0-3}$;

R is phenyl, W-substituted phenyl, naphthyl, W-substituted naphthyl, benzodioxolyl, heteroaryl, W-substituted heteroaryl, benzofused heteroaryl and W-substituted benzofused heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof;

$R^1$ and $R^2$ are independently selected from H or R;

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkylenedioyl, lower alkyl lower alkylenedioyl, allyloxy, —$CF_3$, —$OCF_3$, benzyl, $R^3$-benzyl, benzyloxy, $R^3$-benzyloxy, phenoxy, $R^3$-phenoxy, dioxolanyl, $NO_2$, —$NR^4R^5$, $NR^4R^5$(lower alkyl)-, $NR^4R^5$(lower alkoxy)-, OH, halogeno, —NHC(O)$OR^6$, —NHC(O)$R^6$, $R^7O_2SNH$—, ($R^7O_2S)_2N$—, —$S(O)_2NH_2$, —$S(O)_{0-2}R^4$, tert-butyldimethyl-silyloxymethyl, —C(O)$R^8$,

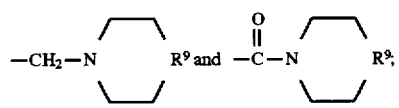

A and D are independently a bond; $C_3$-$C_6$ cycloalkylene; $C_1$-$C_{10}$alkylene; $C_2$-$C_{10}$alkenylene;

$C_2$-$C_{10}$alkynylene; an alkylene, alkenylene or alkynylene chain as defined substituted by one or more substituents independently selected from the group consisting of phenyl, W-substituted phenyl, heteroaryl and W-substituted heteroaryl, wherein heteroaryl is as defined above; an alkylene, alkenylene or alkynylene chain as defined interrupted by one or more groups independently selected from the group consisting of —O—, —S—, —SO—, —$SO_2$—, —$NR_8$, —C(O)—, $C_3$-$C_6$ cycloalkylene, phenylene, W-substituted phenylene, heteroarylene and W-substituted heteroarylene; or an interrupted alkylene, alkenylene or alkynylene chain as defined substituted by one or more substituents independently selected from the group consisting of phenyl, W-substituted phenyl, heteroaryl and W-substituted heteroaryl; or $R^2$-D is selected from the group consisting of halogeno, OH, lower alkoxy, —OC(O)$R^6$, —$NR^4R^5$, —SH and —S(lower alkyl);

$R^3$ is 1–3 groups independently selected from the group consisting of lower alkyl, lower alkoxy, —COOH, $NO_2$, —$NR^4R^5$, OH or halogeno;

$R^4$ and $R^5$ are independently selected from H and lower alkyl;

$R^6$ is lower alkyl, phenyl, $R^3$-phenyl, benzyl or $R^3$-benzyl;

$R^7$ is OH, lower alkyl, phenyl, benzyl, $R^3$-phenyl or $R^3$-benzyl;

$R^8$ is H, OH, alkoxy, phenoxy, benzyloxy,

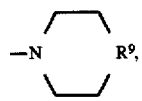

—$NR^4R^5$, lower alkyl, phenyl or $R^3$-phenyl;

$R^9$ is —O—, —$CH^2$—, —NH— or —N(lower alkyl)-;

or Q and $R^2$—D— together form the group

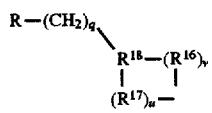

wherein $R^{18}$ is

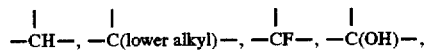
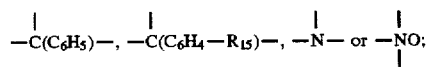

$R^{16}$ and $R^{17}$ are independently selected from the group consisting of —$CH_2$—, —CH(lower alkyl)-, —O(dilower alkyl)-, —CH=CH— and —C(lower alkyl)=CH—; or $R^{18}$ together with an adjacent $R^{16}$, or $R^{18}$ together with an adjacent $R^{17}$, form a —CH=CH— or a —CH=C(lower alkyl)- group;

u and v are independently 0, 1, 2 or 3, provided both are not zero; provided that when $R^{16}$ is —CH=CH— or —O(lower alkyl)=CH—, v is 1; provided that when $R^{17}$ is —CH=CH— or —C(lower alkyl)=CH—, u is 1; provided that when v is 2 or 3, the $R^{16}$'s can be the same or different; and provided that when u is 2 or 3, the $R^{17}$'s can be the same or different; and q is 0, 1, 2, 3, 4, 5 or 6;

comprising reacting a β-(substituted-amino)amide of the formula

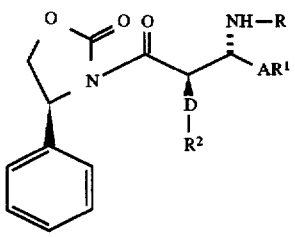

with bistrimethylsilylacetamide and (S)-4-phenyl-2-oxazolidinone tetra n-butylammonium salt.

3. A process of claim 1 wherein the fluoride ion catalyst is a quaternary alkylammonium fluoride salt, a quaternary alkylammonium fluoride salt hydrate, a quaternary arylalkyl-ammonium fluodde salt, a quaternary arylalkyl-ammonium fluoride salt hydrate, a quaternary arylalkyl-alkyl-ammonium fluoride salt, a quaternary arylalkyl-alkyl-ammonium fluoride salt hydrate, or a mixture thereof.

4. A process of claim 1 wherein the fluoride ion catalyst is an alkali metal fluoride salt or hydrate thereof.

5. A process of claim 4 comprising reacting a compound of the formula

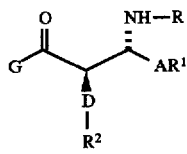

wherein A, D, R, R¹, R², and G are as defined in claim 4, with a silylating agent and a fluoride ion catalyst cyclizing agent.

6. A process of claim 4 comprising reacting a compound of the formula

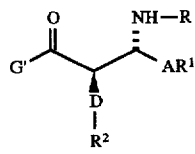

wherein A, D, R, R¹, and R² are as defined in claim 4 and G' is B', wherein B' is a deprotonated chiral auxiliary selected from the group consisting of

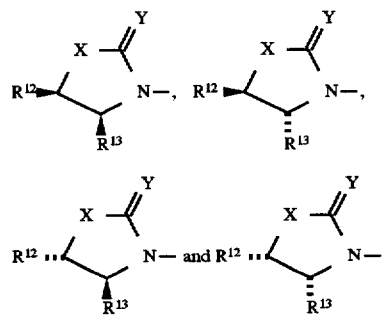

wherein X is —O—, —S— or —N(C₁-C₆alkyl)-; Y is =O or =S; and R¹² and R¹³ are independently selected from the group consisting of C₁-C₆ alkyl, phenyl, naphthyl, substituted phenyl, substituted naphthyl, lower alkoxycarbonyl and benzyl, wherein the substituents on the phenyl and naphthyl are 1–3 substituents selected from the group consisting of lower alkyl, phenyl and benzyl, or wherein one of R¹² or R¹³ is as defined above and the other is hydrogen;

with a a silylating agent and a cyclizing agent which is a monovalent salt of the formula

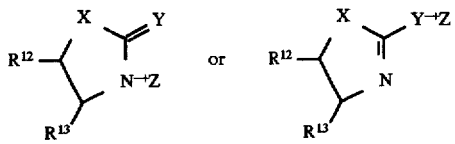

wherein X, Y, R¹² and R¹³ are as defined above or each of R¹² and R¹³ is hydrogen, and Z is selected from the group consisting of quaternary ammonium cations and alkali metals wherein the quaternary ammonium cations are selected from the group consisting of arylalkyl-alkylammonium, aryl-alkylammonium, tetraalkylammonium and mixtures thereof.

7. A process of claim 1 wherein the silylating agent is a silyl-enol ether.

8. A process of claim 1 wherein the silylating agent is bistrimethyisilylacetamide, N-methyl-O-trimethyl silylacetamide or isopropenyloxy trimethylsilane.

9. A process of claim 5 comprising reacting a β-(substituted-amino)amide of the formula

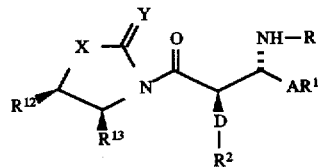

wherein X and Y are each oxygen, R¹² is hydrogen and R¹³ is phenyl, benzyl or isopropyl, with bistrimethylsilylacetamide and with tetra n-butyl-ammonium fluoride, cesium fluoride or a hydrate thereof.

10. A process of claim 1 wherein the fluoride ion catalyst is tetra n-butylammonium fluoride, cesium fluoride, potassium fluoride, or a hydrate thereof.

11. A process for preparing a compound of the formula

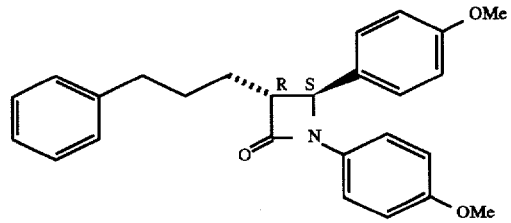

comprising reacting a β-(substituted-amino)amide of the formula

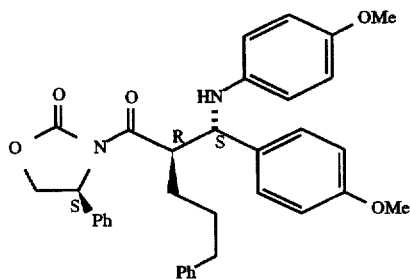
with bistrimethylsilylacetamide and with tetra n-butyl-ammonium fluoride, cesium fluoride or a hydrate thereof.
12. A process for preparing a compound of the formula
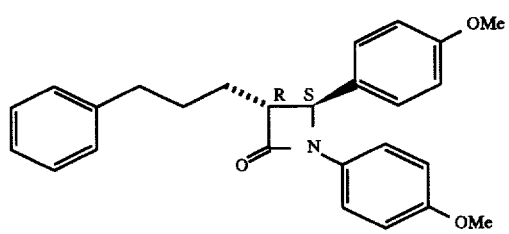
comprising reacting a β-(substituted-amino)amide of the formula
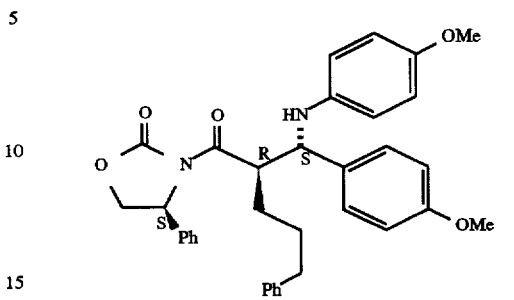
with bistrimethylsilylacetamide and (S)-4-phenyl-2-oxazolidinone tetra n-butylammonium salt.
* * * * *